(12) United States Patent
Serbousek

(10) Patent No.: US 8,641,735 B2
(45) Date of Patent: Feb. 4, 2014

(54) IMPLANTABLE LONGITUDINAL ORTHOPEDIC SUPPORTS FOR ACCOMMODATING MULTIPLE ANATOMICAL SUPPORT REQUIREMENTS

(75) Inventor: Jon Serbousek, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2082 days.

(21) Appl. No.: 11/341,168

(22) Filed: Jan. 27, 2006

(65) Prior Publication Data

US 2007/0186990 A1 Aug. 16, 2007

(51) Int. Cl.
*A61B 17/70* (2006.01)

(52) U.S. Cl.
USPC .......................... 606/259; 606/280; 606/261

(58) Field of Classification Search
USPC ............ 138/135; 606/54, 255, 256, 257, 258, 606/259, 260, 261, 262–278, 280–299, 70, 606/71
See application file for complete search history.

(56) References Cited

U.S. PATENT DOCUMENTS

| | | | |
|---|---|---|---|
| 4,445,513 A * | 5/1984 | Ulrich et al. ................ 606/86 A |
| 4,887,595 A | 12/1989 | Heinig et al. | |
| 5,217,461 A | 6/1993 | Asher et al. | |
| 5,306,275 A * | 4/1994 | Bryan ........................... 606/914 |
| 5,360,429 A | 11/1994 | Jeanson | |
| 5,380,323 A * | 1/1995 | Howland ..................... 606/278 |
| 5,380,324 A * | 1/1995 | Muller et al. ................. 606/256 |
| 5,382,248 A * | 1/1995 | Jacobson et al. ................ 606/60 |
| 5,413,602 A * | 5/1995 | Metz-Stavenhagen .... 623/17.15 |
| 5,470,333 A * | 11/1995 | Ray .............................. 606/261 |
| 5,480,401 A * | 1/1996 | Navas ............................ 606/256 |
| 5,486,174 A | 1/1996 | Fournet-Fayard et al. | |
| 5,507,745 A | 4/1996 | Logroscino et al. | |
| 5,593,407 A * | 1/1997 | Reis .............................. 606/261 |
| 5,593,408 A | 1/1997 | Gayet et al. | |
| 5,620,445 A | 4/1997 | Brosnaham et al. | |
| 5,626,580 A | 5/1997 | Brosnaham | |
| 5,766,174 A * | 6/1998 | Perry ............................. 606/62 |
| 6,296,644 B1 * | 10/2001 | Saurat et al. .................. 606/256 |
| 6,379,359 B1 | 4/2002 | Dahners | |
| 6,485,491 B1 | 11/2002 | Farris et al. | |
| 6,488,685 B1 | 12/2002 | Manderson | |
| 6,620,164 B2 | 9/2003 | Ueyama et al. | |
| 6,645,210 B2 | 11/2003 | Manderson | |
| 6,648,886 B2 | 11/2003 | Nohara et al. | |
| 6,730,090 B2 | 5/2004 | Orbay et al. | |
| 7,314,467 B2 * | 1/2008 | Howland ..................... 606/86 A |
| 2002/0042614 A1 * | 4/2002 | Ueyama et al. ................. 606/61 |
| 2003/0083661 A1 | 5/2003 | Orbay et al. | |
| 2004/0092934 A1 * | 5/2004 | Howland ........................ 606/61 |
| 2004/0092935 A1 | 5/2004 | Manderson | |
| 2005/0149025 A1 * | 7/2005 | Ferrante et al. ................. 606/62 |
| 2008/0234746 A1 * | 9/2008 | Jahng et al. ................... 606/278 |

FOREIGN PATENT DOCUMENTS

| | | |
|---|---|---|
| EP | 0 301 489 A1 | 2/1989 |
| EP | 1 444 958 A | 8/2004 |
| FR | 2 626 460 A | 8/1989 |
| FR | 2 749 155 A1 | 12/1997 |
| WO | WO 2004/089244 A | 10/2004 |

* cited by examiner

*Primary Examiner* — Jan Christopher Merene

(57) ABSTRACT

Elongated members for use in orthopedic procedures for supporting or correcting tissue are disclosed. Embodiments include several sections, some of which are of differing diameters than others, and such sections may be generally rod-shaped or plate-shaped.

14 Claims, 2 Drawing Sheets

IMPLANTABLE LONGITUDINAL ORTHOPEDIC SUPPORTS FOR ACCOMMODATING MULTIPLE ANATOMICAL SUPPORT REQUIREMENTS

This disclosure concerns elongated members used in orthopedic surgery to support bone and other tissue toward healing of injury, correction of deformity, or other reasons. In particular, this disclosure concerns implantable longitudinal connectors constructed to have a varying cross-section along the long axis.

BACKGROUND

In orthopedic surgical procedures, a surgeon may implant a variety of items for the purpose of supporting tissue, fusing tissue together, or maintaining space between or location of tissue to promote healing or correction of deformity. For example, in the spinal surgical field, rods have been connected to vertebrae via hooks, screws and/or clamps in order to support a vertebral section or motion segment(s) in a desired formation. Some such rods may be bent into a configuration approximating the natural or desired curvature of a section of the spine. It can happen, however, that such rods are not easily bent, or are not able to be used with respect to all sections of the spine or other anatomic locations. As another example, spinal surgeons may use short plates to connect two or more vertebrae in order to hold them together and perhaps to facilitate fusion between adjacent vertebrae. Many types of plates do not match or approximate a desired anatomical placement of adjacent vertebrae, which can result in one end of a plate being somewhat distant from a vertebra, while the other end contacts or is substantially nearer another vertebra.

DESCRIPTION OF THE ILLUSTRATED EMBODIMENTS

Figure 1:
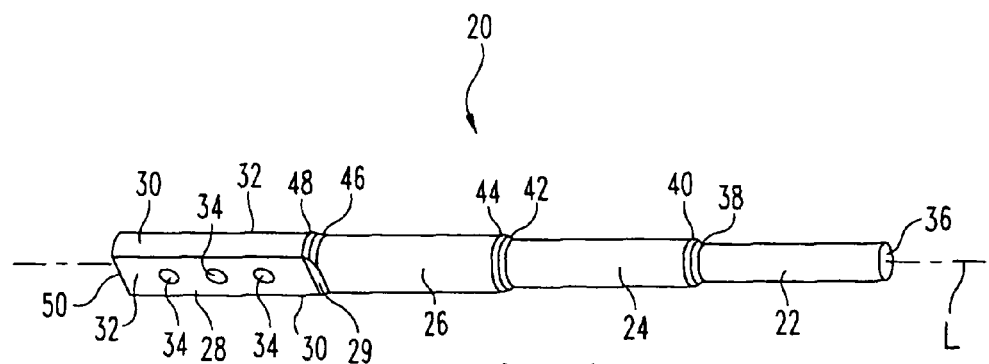
FIG. 1 is a perspective view of an embodiment of an elongated member as disclosed herein.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated devices, and such further applications of the principles of the disclosure as illustrated therein, being contemplated as would normally occur to one skilled in the art to which the disclosure relates.

Referring now generally to the figures, there are shown embodiments of an elongated member for use in orthopedic surgery, such as spinal corrective or therapeutic surgery. Each of the embodiments shown has similarities to the others, and therefore similar numbers will be used in this disclosure to indicate the same or similar features.

Elongated member 20 (FIG. 1) includes four sections 22, 24, 26 and 28. In that embodiment, each of sections 22, 24 and 26 is substantially a cylinder having a uniform diameter. The diameter of section 22 is less than that of section 24, and the diameter of section 24 is less than that of section 26. Section 28 is a plate section, in contrast to the rod sections of sections 22, 24, and 26. A sloped surface 29, which may be substantially planar, concave, or otherwise configured, is between sections 26 and 28, and such a surface 29 may be adjacent both sides of section 28. Section 28 has two portions 30 that form part of a cylinder having a diameter. The diameter of section 28, in the illustrated embodiment, is larger than the diameter of section 26. Section 28 further includes two substantially flat surfaces 32 that are opposed to each other and may abut surfaces 29, and holes 34 extend from one surface 32 to the other surface 32. A plate section such as section 28 may include one or more openings, which may be of relatively small diameter such as holes 34, or may be somewhat larger and/or elongated. For example, one or more slots could extend along some or substantially all of the length of section 28. In one particular embodiment, a plate section such as section 28 may have a width dimension substantially perpendicular to central longitudinal axis L, which is greater than half of the diameter of section 28.

One end 36 of section 22 forms an end of elongated member 20. Another end 38 of section 22 is adjoined to an end 40 of section 24. Similarly, another end 42 of section 24 is adjoined to an end 44 of section 26, and another end 46 of section 26 is adjoined to section 28. The other end 48 of section 28 forms the other end of elongate member 20, in the illustrated embodiment. Ends 38 and 40 taken together (and surfaces 29, if present) may be considered a transitional portion that narrows the larger diameter of section 24 down to the smaller diameter of section 22. Similarly, ends 42 and 44 taken together and ends 46 and 48 taken together may also be considered a comparable transitional portion. An end 50 of section 28 may form an end of elongated member 20. In the illustrated embodiment, these transitional portions are substantially conical in configuration, in which the narrowing is substantially constant along the longitudinal axis. It is understood that such transitional portions may be otherwise configured, for example having a concave or convex form, or both, when viewed in longitudinal cross-section, or being stepped from one diameter directly to another.

It is to be understood that variations of the above-described parameters are possible. For example, in other embodiments sections 22, 24 and/or 26 may have a configuration other than cylindrical, for example part-cylindrical, flat or otherwise shaped. Further, the sections may be otherwise arranged, for example by having a plate section as a medial section (e.g. sections 24 and 26) rather than an end section (e.g. sections 22 and 28). In the illustrated embodiment, each of sections 22, 24, 26, 28 has a central longitudinal axis, which are collinear with each other and shown as axis L in FIG. 1.

In use, elongated member 20 may be placed adjacent bone or other tissue so as to provide orthopedic support or correction. In the area of spinal surgery, for example, elongated member 20 may be fixed to one or more vertebrae or spinal segments. In the illustrated embodiment of elongated member 20, rod sections 22, 24 and/or 26 may be connected to bone screws, hooks, clamps, or other apparatus that are attached to or connected to bone. Examples of such apparatus are disclosed in U.S. Pat. Nos. 5,005,562; 5,797,911 and 6,280,442, each of which is incorporated herein by reference in its entireties. If an end section is a rod section, as in the illustrated embodiment of elongated member 20 in which section 22 is a rod section, normally such end section will be connected to a bone attachment apparatus. A plate section, such as section 28, is connected to a vertebra via screws (not shown) inserted through one or more of openings 34 and into bone tissue. Alternatively, one or more wire, cable, fiber or other filamentary elements could be inserted through one or more of openings 34 and around bone or other tissue to anchor plate section 28. Hook or clamp members could also be used to fix plate section 28 with respect to a vertebra.

Prior to or after connection to bone or other tissue, elongated member 20 may be bent to conform to a desired curvature. In some embodiments, such bending may take place at or adjacent one or more transitional portions of elongated member 20, as the change in diameter provides a convenient and somewhat easier place to bend. Elongated member 20 can be bent so as to form a curve or shape substantially in one plane, or in more than one plane, as the therapeutic or corrective need may dictate. For example, one or more sections of elongated member 20 could be bent substantially around one or more axes perpendicular to axis L and parallel to each other, forming an approximately C-shaped or S-shaped curve. Alternatively, one or more sections of elongated member 20 could be bent substantially around axes that are perpendicular to axis L and to each other.

The illustrated embodiment of elongated member 120 includes an end section 122, a medial section 124 and an end section 126. Section 122 is configured similarly to section 28 of elongated member 20, having two portions 130 that form part of a cylinder having a diameter, and two substantially flat surfaces 132 that are opposed to each other. Holes 134 extend from one surface 132 to the other surface 132. A plate section such as section 122 may include one or more openings, which may be of relatively small diameter such as holes 134, or may be somewhat larger and/or elongated. For example, one or more slots could extend along some or substantially all of the length of section 122.

Section 124 is a plate section similar to plate section 122, having two sides 130a that form part of a cylinder having a diameter. Flat surfaces 132a are opposed to each other, and in the illustrated embodiment are coplanar with surfaces 132 of section 122. In other words, in a particular embodiment sections 122 and 124 have essentially one flat surface 132/132a between them on each side of elongated member 120. The diameter of the substantially cylindrical sides 130a is smaller than the diameter of substantially cylindrical sides 130 of section 122, in the illustrated embodiment. Further, section 124 may include one or more openings, which may be of relatively small diameter such as holes 134, or may be one or more somewhat larger and/or elongated slots or other openings. In the illustrated embodiment, holes 134 in sections 122 and 124 are substantially uniform between the sections, although in other embodiments the size, shape or other configuration aspects of one or more holes in each section 122 and 124 could differ from each other or from those in the other section.

Section 126 is a rod section similar in configuration to section 22 of elongated member 20. Section 126 is substantially cylindrical in the illustrated embodiment, having a diameter that is larger than that of section 124 and approximately equal to that of section 122. A sloped surface 129 extends between surface 132a and the outer surface of section 126 on each side of elongated member 120. Sloped surface 129 is concave in the illustrated embodiment, and may be substantially planar or otherwise configured in other embodiments.

One end 136 of section 122 forms an end of elongated member 120. Another end 138 of section 122 is adjoined to an end 140 of section 124. Similarly, another end 142 of section 124 is adjoined to an end 144 of section 26, and the other end 150 of section 126 forms the other end of elongate member 120, in the illustrated embodiment. Ends 138 and 140 taken together may be considered a transitional portion that narrows the larger diameter of section 122 down to the smaller diameter of section 124. Ends 142 and 144 taken together may also be considered a transitional portion, which widens the smaller diameter of section 124 to the larger diameter of section 126. In the illustrated embodiment, these transitional portions are curved in configuration, being convex adjacent sections of larger diameter (sections 122 and 126 in this embodiment) and concave adjacent sections of smaller diameter (section 124 in this embodiment). In other embodiments, such narrowing or widening may be substantially constant along the longitudinal axis, for example one or more substantially conical surfaces. Such transitional portions may be otherwise configured, for example having only a concave or convex form when viewed in longitudinal cross-section, or being stepped from one diameter directly to another. An end 150 of section 126 forms an end of elongated member 120.

Figure 2:
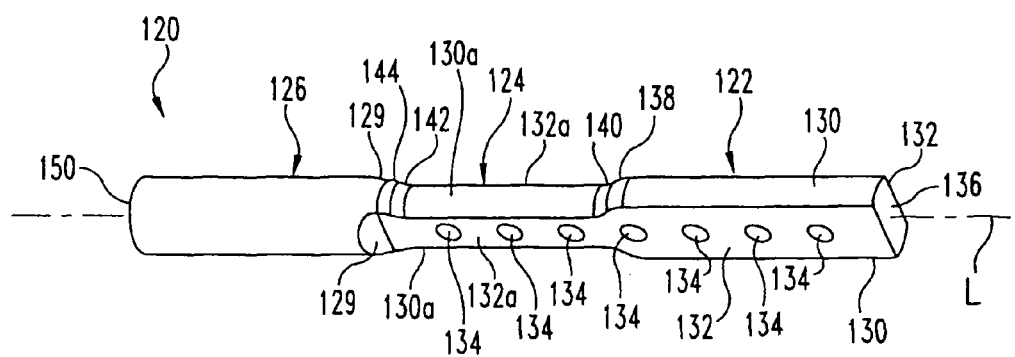
FIG. 2 is a perspective view of another embodiment of an elongated member as disclosed herein.

Variations of the above-described parameters are possible, as suggested above with respect to elongated member 20. For example, in other embodiments sections 122, 124 and/or 126 may be differently configured, and may be otherwise arranged. In the illustrated embodiment, each of sections 122, 124, 126 has a central longitudinal axis, which are collinear with each other and shown as axis L in FIG. 2.

Elongated member 120 is used in a similar manner as elongated member 20. As described above, section 126 may be connected to bone screws, hooks, clamps, or other apparatus that are attached to or connected to bone. Plate sections 122 and 124 may be connected to a vertebra via screws (not shown) inserted through one or more of openings 134 and into bone tissue. Alternatively, one or more wire, cable, fiber or other filamentary elements could be inserted through one or more of openings 134 and around bone or other tissue to anchor one or both of plate sections 122 and 124. Hook or clamp members could also be used to fix one or both of plate sections 122 and 124 with respect to a vertebra. In some embodiments, medial section 124 need not be attached to tissue, with sections 122 and 126 being connected to vertebrae (as one example) so that tissue adjacent section 124 is compressed or distracted for correction, healing or support.

Prior to or after connection to bone or other tissue, elongated member 120 may be bent to conform to a desired curvature. In some embodiments, such bending may take place at or adjacent one or more transitional portions of elongated member 120, as the change in diameter provides a convenient and somewhat easier place to bend. Elongated member 120 can be bent so as to form a curve or shape substantially in one plane, or in more than one plane, as discussed previously.

Elongated member 220, in the illustrated embodiment, is quite similar to the illustrated embodiment of elongated member 120, except that end section 222 is a rod section as opposed to the plate section 122 of elongated member 120. Medial section 224 is essentially similar to section 124 of elongated member 120, having two portions 230 that form part of a cylinder having a diameter, and two substantially flat surfaces 232 that are opposed to each other. Holes 234 extend from one surface 232 to the other surface 232. Section 224 may include one or more openings, which may be of relatively small diameter such as holes 234, or may be somewhat larger and/or elongated, as previously described.

Sections 222 and 226 are rod sections similar in configuration to section 126 of elongated member 120, e.g. substantially cylindrical in the illustrated embodiment, having diameters that are approximately equal to each other and larger than the diameter of section 224. The diameter of section 226 may be somewhat larger or smaller than that of section 222. A sloped surface 229 extends between surface 232 and the outer surface of sections 222 and 226 on each side of elongated member 220. Sloped surfaces 229 are concave in the illustrated embodiment, and may be substantially planar or otherwise configured in other embodiments.

One end 236 of section 222 forms an end of elongated member 220. Another end 238 of section 222 is adjoined to an end 240 of section 224. Similarly, another end 242 of section 224 is adjoined to an end 244 of section 26, and the other end 250 of section 226 forms the other end of elongate member 220, in the illustrated embodiment. Ends 238 and 240 taken together may be considered a transitional portion that narrows the larger diameter of section 222 down to the smaller diameter of section 224. Ends 242 and 244 taken together may also be considered a transitional portion, which widens the smaller diameter of section 224 to the larger diameter of section 226. In the illustrated embodiment, these transitional portions are curved, being convex adjacent sections of larger diameter (sections 222 and 226 in this embodiment) and concave adjacent sections of smaller diameter (section 224 in this embodiment). In other embodiments, such narrowing or widening may be substantially constant along the longitudinal axis, for example one or more substantially conical surfaces. Such transitional portions may be otherwise configured, for example having only a concave or convex form when viewed in longitudinal cross-section, or being stepped from one diameter directly to another.

Figure 3:
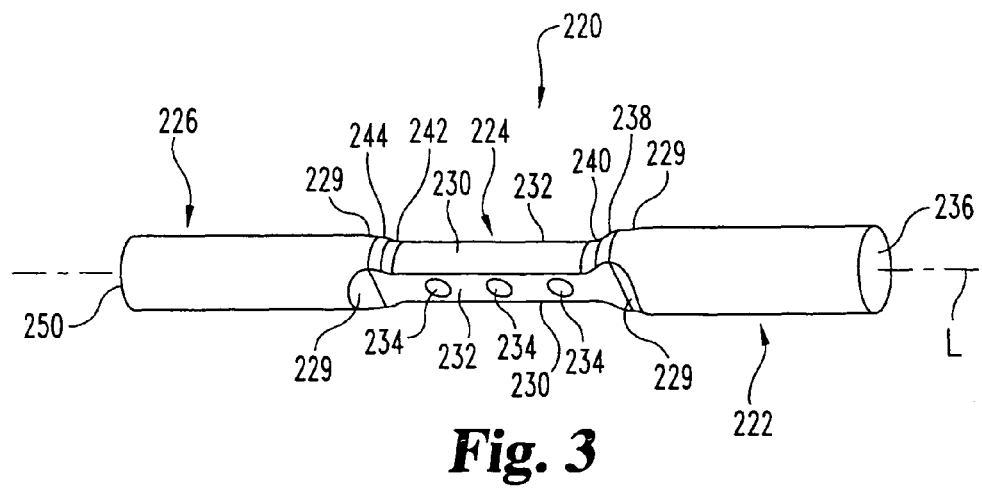
FIG. 3 is a perspective view of a further embodiment of an elongated member as disclosed herein.

Variations of the above-described parameters are possible, as suggested above with respect to elongated member 20 and 120. For example, in other embodiments sections 222, 224 and/or 226 may be differently configured, and may be otherwise arranged. In the illustrated embodiment, each of sections 222, 224, 226 has a central longitudinal axis, which are collinear with each other and shown as axis L in FIG. 3.

Elongated member 220 is used in a similar manner as elongated member 20 and 120. As described above, sections 222 and 226 may be connected to bone screws, hooks, clamps, or other apparatus that are attached to or connected to bone. Plate section 224 may be connected to a vertebra via screws (not shown) inserted through one or more of openings 234 and into bone tissue. Alternatively, one or more wire, cable, fiber or other filamentary elements could be inserted through one or more of openings 234 and around bone or other tissue to anchor plate section 224. Hook or clamp members could also be used to fix plate section 224 with respect to a vertebra. In some embodiments, medial section 224 need not be attached to tissue, with sections 222 and 226 being connected to vertebrae (as one example) so that tissue adjacent section 224 is compressed or distracted for correction, healing or support.

Prior to or after connection to bone or other tissue, elongated member 220 may be bent to conform to a desired curvature. In some embodiments, such bending may take place at or adjacent one or more transitional portions of elongated member 220, as the change in diameter provides a convenient and somewhat easier place to bend. Elongated member 220 can be bent so as to form a curve or shape substantially in one plane, or in more than one plane, as discussed previously.

Elongated member 320, in the illustrated embodiment, is quite similar to the illustrated embodiment of elongated member 120, except that medial section 324 is a rod section as opposed to the plate section 124 of elongated member 120. End section 322 is essentially similar to section 122 of elongated member 120, having two portions 330 that form part of a cylinder having a diameter, and two substantially flat surfaces 332 that are opposed to each other. Holes 334 extend from one surface 332 to the other surface 332. In other embodiments, section 322 may include one or more openings, which may be of relatively small diameter such as holes 334, or may be somewhat larger and/or elongated, as previously described. Medial section 324 is essentially similar to section 22 of elongated member 20, being substantially cylindrical and having a diameter. End section 326, like section 226 of elongated member 220, is also substantially cylindrical and has a diameter that is larger than the diameter of section 324 and approximately equal to the diameter of section 322, in the illustrated embodiment. The diameter of section 326 may be somewhat larger or smaller than that of section 322.

One end 336 of section 322 forms an end of elongated member 320. Another end 338 of section 322 is adjoined to an end 340 of section 324. Similarly, another end 342 of section 324 is adjoined to an end 344 of section 326, and the other end 350 of section 326 forms the other end of elongate member 320, in the illustrated embodiment. Ends 338 and 340 taken together may be considered a transitional portion that narrows the larger diameter of section 322 down to the smaller diameter of section 324. Ends 342 and 344 taken together may also be considered a transitional portion, which widens the smaller diameter of section 324 to the larger diameter of section 326. In the illustrated embodiment, these transitional portions are curved, being convex adjacent sections of larger diameter (sections 322 and 326 in this embodiment) and concave adjacent sections of smaller diameter (section 324 in this embodiment). A portion 332a of surfaces 332 may also form part of or abut one or both of ends 338 and 340. In other embodiments, such narrowing or widening may be substantially constant along the longitudinal axis, for example one or more substantially conical surfaces. Such transitional portions may be otherwise configured, for example having only a concave or convex form when viewed in longitudinal cross-section, or being stepped from one diameter directly to another.

Figure 4:
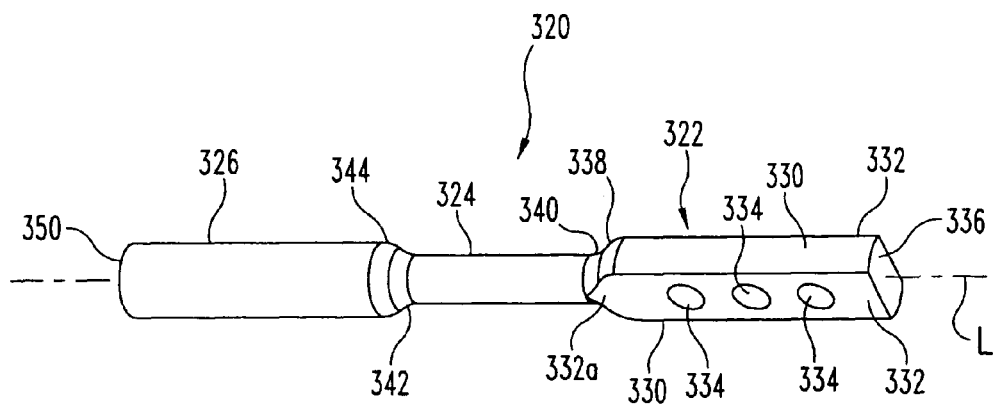
FIG. 4 is a perspective view of another embodiment of an elongated member as disclosed herein.

Variations of the above-described parameters are possible, as suggested above with respect to elongated member 20, 120 and 220. For example, in other embodiments sections 322, 324 and/or 326 may be differently configured, and may be otherwise arranged. In the illustrated embodiment, each of sections 322, 324, 326 has a central longitudinal axis, which are collinear with each other and shown as axis L in FIG. 4.

Elongated member 320 is used in a manner similar to those discussed above with respect to elongated members 20, 120 and 220. Sections 324 and/or 326 may be connected to bone screws, hooks, clamps, or other apparatus that are attached to or connected to bone. Plate section 322 may be connected to a vertebra via screws (not shown) inserted through one or more of openings 334 and into bone tissue. Alternatively, one or more wire, cable, fiber or other filamentary elements could be inserted through one or more of openings 334 and around bone or other tissue to anchor plate section 324. Hook or clamp members could also be used to fix plate section 324 with respect to a vertebra. In some embodiments, medial section 324 is not attached to apparatus or tissue, with sections 322 and 326 being connected to vertebrae (as one example) so that tissue adjacent section 324 is compressed or distracted for correction, healing or support.

Prior to or after connection to bone or other tissue, elongated member 320 may be bent to a desired curvature. In some embodiments, such bending may take place at or adjacent one or more transitional portions of elongated member 320, as the change in diameter provides a convenient and somewhat easier place to bend. Elongated member 320 can be bent so as to form a curve or shape substantially in one plane, or in more than one plane, as discussed previously.

Figure 5:
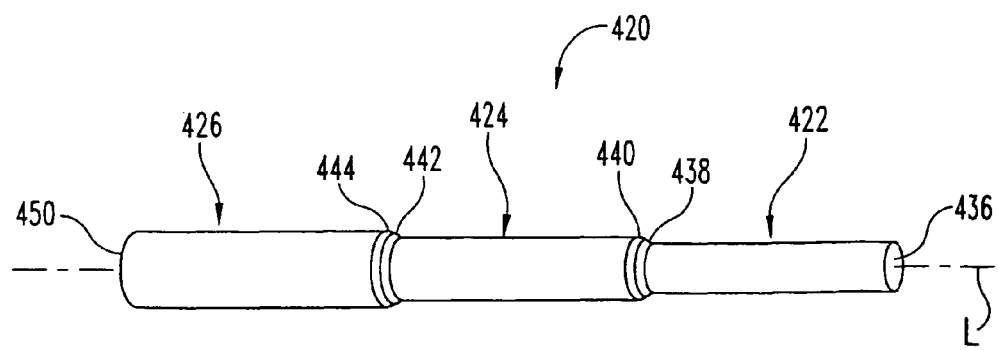
FIG. 5 is a perspective view of yet a further embodiment of an elongated member as disclosed herein.

Elongated member 420 (FIG. 5) has three sections 422, 424 and 426 that are, in the illustrated embodiment, essentially similar to sections 22, 24 and 26 of elongated member 20. Thus, in that embodiment each of sections 422, 424 and 426 is substantially a cylinder having a uniform diameter. The diameter of section 422 is less than that of section 424, and the diameter of section 424 is less than that of section 426.

One end 436 of section 422 forms an end of elongated member 420. Another end 438 of section 422 is adjoined to an end 440 of section 424. Similarly, another end 442 of section 424 is adjoined to an end 444 of section 426. The other end 450 of section 426 forms the other end of elongate member 420, in the illustrated embodiment. Ends 438 and 440 taken together may be considered a transitional portion that narrows the larger diameter of section 424 down to the smaller diameter of section 422. Similarly, ends 442 and 444 taken together may also be considered a comparable transitional portion. These transitional portions can be substantially conical in configuration, in which the narrowing is substantially constant along the longitudinal axis. Such transitional portions could be otherwise configured, for example having a concave or convex form, or both, when viewed in longitudinal cross-section, or being stepped from one diameter directly to another. An end 450 of section 426 forms an end of elongated member 420.

It is to be understood that variations of the above-described parameters are possible, as discussed above with respect to elongated member 20. In the illustrated embodiment, each of sections 422, 424, 426 has a central longitudinal axis, which are collinear with each other and shown as axis L in FIG. 5. Elongated member 420 is used in essentially the same manner discussed above with respect to elongated member 20. In particular, sections 422, 424 and/or 426 may be connected to bone screws, hooks, clamps, or other apparatus that are attached to or connected to bone. Prior to or after connection to bone or other tissue, elongated member 420 may be bent to conform to a desired curvature. In some embodiments, such bending may take place at or adjacent one or more transitional portions of elongated member 420, as the change in diameter provides a convenient and somewhat easier place to bend. Elongated member 420 can be bent so as to form a curve or shape substantially in one plane, or in more than one plane, as the therapeutic or corrective need may dictate. For example, one or more sections of elongated member 420 could be bent substantially around one or more axes perpendicular to axis L and parallel to each other, forming an approximately C-shaped or S-shaped curve. Alternatively, one or more sections of elongated member 420 could be bent substantially around axes that are perpendicular to axis L and to each other.

A single one of the elongated members 20, 120, 220, 320 or 420 can be used in a particular surgery or surgical site, or multiple elongated members can be used. For example, an embodiment of elongated member 20 can be attached to a vertebra by its plate section 28, and to at least one other vertebra by connecting one or more of rod sections 22, 24 and 26 to screws, hooks or other apparatus adjoining or inserted into such vertebra(e). On another side of the vertebrae, alongside elongated element 20, or otherwise positioned according to the desire of the surgeon and the surgical necessity, another elongated member (e.g. member 120) can be attached as described above to provide additional stability. Rod sections of the elongated members disclosed herein can be connected via transverse connectors to rod sections or other parts of other elongated members in spinal surgery. Numerous different configurations of attachment of one or more elongated members to the spine or other tissue are possible.

Further, the embodiments of elongated members disclosed herein can be used to bridge multiple levels of the spine. For example, when therapy or correction is needed in an area of the spine that includes both cervical and thoracic vertebrae, the disclosed elongated members can be attached to the affected spinal areas so that thinner sections are attached to or adjacent smaller cervical vertebrae and thicker sections are attached to or adjacent larger thoracic vertebrae. In other examples, an elongated member with a relatively thin medial section can be used to provide flexibility as well as stability to a vertebral segment, while somewhat thicker end sections are secured to adjacent vertebrae. The disclosed elongated members can be used in all types of orthopedic procedures in which a rod, bar or plate is indicated. In orthopedic situations in which one area requires a certain size or stiffness of rod or plate, while another area requires somewhat different support characteristics, the above-described elongated members can be used with success.

As particular examples, the illustrated embodiment of elongated member 20 could be configured so that plate section 28 can be attached to the occiput, and the stiffness of elongated member 20 is reduced due to the narrowing diameter of the other sections. The illustrated embodiment of elongated member 120 is one in which the stiffness depends on the bending plane or axis, since it is not of uniform thickness in all directions, and it could also be configured so that plate section 122 can be attached to the occiput. The other illustrated embodiments, and other embodiments not specifically illustrated herein, have similar abilities to provide various stiffness and bending characteristics as well as to link to a variety of apparatus or tissues. The disclosed elongated members may provide more or better load-sharing among vertebrae or other tissue, for example at a vertebral fusion site, and promote better healing. They may also enable maintenance of limited and/or controlled joint motion during healing, and low profile attachment or connection to bone or other tissue.

The devices of the present invention are preferably constructed of sturdy bio-compatible materials, such as stainless steel, titanium, certain plastics, or other known materials.

While the disclosure has been illustrated and described in detail in the drawings and foregoing description, the same is to be considered as illustrative and not restrictive in character, it being understood that only embodiments have been shown and described and that all changes and modifications that come within the spirit of the disclosure are desired to be protected.

What is claimed is:

1. An apparatus comprising:
   an implantable elongated member having a first section, a second section and a third section each extending along a longitudinal axis;
   said first section having a first end and an oppositely positioned second end and including at least a portion extending from said first end to said second end that is substantially cylindrical with a first outer diameter;
   said second section having a first and second end, said first end of said second section and said second end of said first section defining a first transition portion thereby connecting said first end of said second section with said second end of said first section, said second section having at least a portion that is substantially cylindrical with a second outer diameter;
   said third section having a first and second end, said first end of said third section and said second end of said second section defining a second transition portion thereby connecting said first end of said third section with said second end of said second section, said third section having at least a portion that is substantially cylindrical with a third outer diameter;

wherein the second outer diameter of said second section is unequal to at least one of said first outer diameter of said first section and said third outer diameter of said third section; and wherein said first section is an end of said elongated member and includes a plate section between said first and second ends of said first section, said plate section having opposite first and second flat surfaces and at least one opening extending from said first flat surface to said second flat surface; and wherein said first and second flat surfaces of said plate section are axially connected directly to said first end of said second section by said first transition portion.

2. The apparatus of claim 1, wherein said plate section has opposite first and second cylindrical surfaces each extending from said first flat surface to said second flat surface and together defining said first outer diameter.

3. The apparatus of claim 1, wherein each of said first, second and third sections has a central longitudinal axis, and wherein said central longitudinal axes of said first, second and third sections are collinear with one another.

4. The apparatus of claim 3, wherein said first and second flat surfaces extend axially along said central longitudinal axis to said first end of said first section.

5. The apparatus of claim 1, wherein said first outer diameter of said first section is greater than said second outer diameter of said second section, and said second outer diameter of said second section is greater than said third outer diameter of said third section.

6. The apparatus of claim 1, wherein said first outer diameter of said first section is substantially uniform from said first end to said second end of said first section; and wherein said second outer diameter of said second section is substantially uniform from said first end to said second end of said second section; and wherein said third outer diameter of said third section is substantially uniform from said first end to said second end of said third section.

7. The apparatus of claim 1, wherein said first transition portion includes:

a first sloped surface abutting said first flat surface and extending to said first end of said second section; and a second sloped surface abutting said second flat surface and extending to said first end of said second section.

8. An apparatus comprising:

an implantable elongated member having a first section, a second section and a third section;

said first section having a first and second end and at least a portion that is substantially cylindrical with a diameter;

said second section having a first and second end, said first end of said second section and said second end of said first section defining a first tapered transition portion thereby connecting said first end of said second section with said second end of said first section, said second section having at least a portion that is substantially cylindrical with a diameter;

said third section having a first and second end, said first end of said third section and said second end of said second section defining a second tapered transition portion thereby connecting said first end of said third section with said second end of said second section, said third section having at least a portion that is substantially cylindrical with a diameter;

wherein the diameter of said second section is unequal to at least one of said diameter of said first section and said diameter of said third section; and wherein at least one of said sections includes a plate section extending from said first end to said second end of said at least one section, said plate section having first and second opposed flat surfaces and at least one opening extending between said surfaces and said other sections lying in line with each other and said plate section on the same longitudinal axis as said plate section.

9. The apparatus of claim 8, wherein said surfaces have a width dimension, said width dimension having a direction substantially perpendicular to a longitudinal axis of said plate section, that is greater than half the diameter of said plate section; and wherein said at least one opening extends through said plate section from a first of said flat surfaces to a second of said flat surfaces.

10. An apparatus comprising:

an implantable elongated member extending from a first end to a second end and having a first section, a second section and a third section each extending along a longitudinal axis;

said first section having a first and second end and at least a portion that is substantially cylindrical with a substantially uniform first outer diameter from said first end to said second end of said first section;

said second section having a first and second end, said first end of said second section and said second end of said first section defining a first tapered transition portion thereby connecting said first end of said second section with said second end of said first section, said second section having at least a portion that is substantially cylindrical with a substantially uniform second outer diameter from said first end to said second end of said second section;

said third section having a first and second end, said first end of said third section and said second end of said second section defining a second tapered transition portion thereby connecting said first end of said third section with said second end of said second section, said third section having at least a portion that is substantially cylindrical with a substantially uniform third outer diameter from said first end to said second end of said third section;

wherein said first, second and third sections are each rod sections, each forming substantially a complete cylinder, and wherein the first outer diameter of said first section is greater than the second outer diameter of said second section, and the second outer diameter of said second section is greater than the third outer diameter of said third section; and wherein said second end of said third section is said second end of said elongated member.

11. The apparatus of claim 10, further comprising a fourth section adjoining said first sections, said fourth section being a plate section having opposite first and second flat surfaces and at least one opening extending from said first flat surfaces to said second flat surface, and wherein said first and second flat surfaces of said plate section are axially connected directly to said first end of said first section by a third tapered transition portion.

12. The apparatus of claim 11, wherein said plate section has opposite first and second cylindrical surfaces each extending from said first flat surface to said second flat surface and defining a fourth outer diameter.

13. The apparatus of claim 11, wherein each of said first, second, third and fourth sections has a central longitudinal axis, and wherein said central longitudinal axes of said first, second, third and fourth sections are collinear with one another.

14. An apparatus comprising:
an implantable elongated member having a first section, a second section and a third section;
said first section having a first and second end and at least a portion that is substantially cylindrical with a diameter;
said second section having a first and second end, said first end of said second section and said second end of said first section defining a first tapered transition portion thereby connecting said first end of said second section with said second end of said first section, said second section having at least a portion that is substantially cylindrical with a diameter;
said third section having a first and second end, said first end of said third section and said second end of said second section defining a second tapered transition portion thereby connecting said first end of said third section with said second end of said second section, said third section having at least a portion that is substantially cylindrical with a diameter;
wherein the diameter of said second section is unequal to at least one of said diameter of said first section and said diameter of said third section; and
wherein said first section is an end of said elongated member and is a plate section having first and second opposed flat surfaces and at least one opening extending between said surfaces and transversely through said substantially cylindrical portion of said first section; and
wherein each of said sections has a central longitudinal axis, said substantially cylindrical portion of said first section extends along said axis of said first section, and said axes of said sections are collinear.

* * * * *